United States Patent [19]

Otani et al.

[11] Patent Number: 5,561,126
[45] Date of Patent: Oct. 1, 1996

[54] 4-OXA-1-AZABICYCLO [3,2,0] HEPTAN-7-ONE DERIVATIVES AS ANTITUMOR AGENTS

[75] Inventors: Toshio Otani; Shinji Oie; Hiroshi Matsumoto, all of Iokushima, Japan; Mark Tempest, Edmonton, Canada; Ronald Micetich, Sherwood Park, Canada; Rajeshwar Singh; Tomohiro Yamashita, both of Edmonton, Canada

[73] Assignees: Taiho Pharmaceutical Co., Ltd., Tokyo, Japan; Synphar Laboratories, Inc., Edmonton, Canada

[21] Appl. No.: 362,490

[22] PCT Filed: Jul. 8, 1993

[86] PCT No.: PCT/GB93/01435

§ 371 Date: Mar. 16, 1995

§ 102(e) Date: Mar. 16, 1995

[87] PCT Pub. No.: WO94/01109

PCT Pub. Date: Jan. 20, 1994

[30] Foreign Application Priority Data

Jul. 9, 1992 [GB] United Kingdom ............... 9214603

[51] Int. Cl.$^6$ ................................................ H61K 31/395
[52] U.S. Cl. ................................................ 514/210
[58] Field of Search ................................................ 514/210

[56] References Cited

U.S. PATENT DOCUMENTS 4,093,626  6/1978  Hunt ........................................ 260/307

FOREIGN PATENT DOCUMENTS 1515241  6/1978  United Kingdom ................ 514/210

OTHER PUBLICATIONS

D. Hoppe et al, *Tetrahedron*, "Enantioselective Synthesis of the fungicide beta–lactam antibiotic . . . ", vol. 43, No. 11, 1987, pp. 2467–2474.

T. Konosu et al, *Chem. Pharm. Bull.*, "Enantiocontrolled synthesis of the antifungal beta–lactam . . . ", vol. 39, No. 9, 1991, pp. 2212–2215.

*Primary Examiner*—Jerome D. Goldberg
*Attorney, Agent, or Firm*—Nikaido, Marmelstein, Murray & Oram LLP

[57] ABSTRACT

The present invention relates to the use of 4-oxa-1-azabicyclo [3,2,0] heptan-7-one derivatives of formula (I) or a pharmaceutically acceptable salt thereof, as antitumor agents.

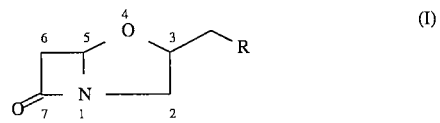

Wherein R is
—OCOR$_1$ group wherein R$_1$ is hydrogen atom, a C$_{1-9}$ alkyl group which may be substituted by either one or two substituents selected together from halogen atom, hydroxy, carboxy group or (3RS,5SR)-(4-oxo-1-azabicyclo[3,2,0]heptan-7-one-3-yl) methyloxycarbonyl, a C$_{2-17}$ alkenyl group, which may be substituted by carboxy group or (3RS,5SR)-(4-oxa-1-azabicyclo [3,2,0]heptan-7-one-3-yl)methyloxycarbonyl, A C$_{2-4}$ alkynyl group, a C$_{3-6}$ cycloalkyl group which may be substituted by carboxy group or phenyl group which may have 1, 2 or 3 substituents selected from the group consisting of cyano group, halogen atom, C$_{1-6}$ alkoxy group which may be substituted by carboxy group, C$_{1-6}$ alkyl group, amino group or hydroxy group.

—OR$_2$ wherein R$_2$ is a hydrogen atom or benzyl group which may be substituted by 1 or 2 C$_{1-6}$ alkoxy group.

—S(O)$_n$R$_3$ wherein R$_3$ is phenyl group or a benzyl group which may be substituted by C$_{1-6}$ alkyl group, n is 0, 1, or 2;

or —CH$_2$OH.

6 Claims, No Drawings

4-OXA-1-AZABICYCLO [3,2,0] HEPTAN-7-ONE DERIVATIVES AS ANTITUMOR AGENTS

The present invention relate to an antitumor composition comprising an effective amount of 4-oxo-1-azabicyclo[3,2,0] heptan-7-one derivatives and a pharmaceutically acceptable carrier.

BACKGROUND OF THE INVENTION

Since the isolation and structure elucidation of natural β-lactamase inhibitor clavulanic acid, [Antimicrobial Agents and Chemotherapy, 11, 852 (1977)], as metabolized product of streptomyces clavuligerus, a number of exploratory efforts have been made to isolate another antibiotics. On the other hands, several synthetic studies also have been done for the β-lactam compounds which have 4-oxa-1-azabicyclo[3,2,0] heptan-7-one (oxapenam) skeletons [DT2702091 A1, EP 0057664 A2, DT 2725690 A1, British Patent 1585661, J. Chem. Soc. Perkin Trans I, 2222 (1980), J. Antibiotics, 26, 217 (1983), J. Org. Chem. 50, 3457–3462 (1985), J. Antibiotics, 29, 510 (1986), ibid, 29, 516 (1987), Tetrahedron, 2467 (1987), Chem. Pharm. Bull., 39, 2813–2818 (1991)].

However, in most case, attention were paid to their strong antibacterial, antifungal and β-lactamase inhibitory activities.

We paid attention to the cytotoxic activities of G0069A (JP 61-212587) and Tü1718 (DE 3727651 A1), produced by genus Streptomyces and have been trying to develop them as antitumor agents. However, there were lots of difficulties to obtain these compounds in large scale. For example, only 20 mg of G0069A was isolated from 10 L of fermentation broth even after under well controlled fermentation technique and suitable experimental conditions.

G0069A is chemically very unstable. Isolation process required very complex and special technique and should be done in dark at low temperature. In addition to the complexity in isolation of G0069A from fermentation broth, the synthetic approach is also seemed to be extremely difficult multistep process because they have 5 asymmetric centers and dipeptide side chain. Therefore, it is necessary to get compounds which are relatively easy to synthesis, have shorter chain than G0069A, chemically stable and have strong antitumor activity.

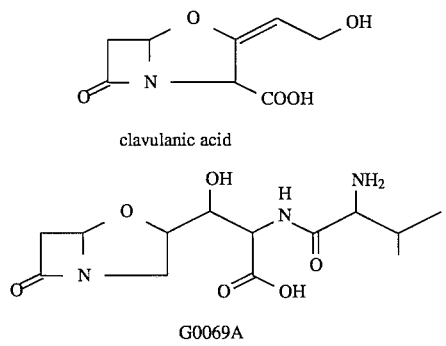

clavulanic acid

G0069A

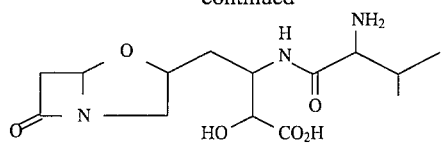

T01718

SUMMARY OF THE INVENTION

The present invention relates to an antitumor composition comprising an effective amount of the 4-oxa-1-azabicyclo [3,2,0]heptan-7-one derivative represented by the formula I or a pharmaceutically acceptable salt thereof

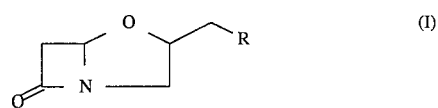

and a pharmaceutically acceptable carrier.

Wherein R is

—$OCOR_1$ wherein $R_1$ is hydrogen atom, a $C_{1-9}$ alkyl group which may be substituted by either one or two substitutents selected together from halogen atom, hydroxy, carboxy group or (3RS,5SR)-(4-oxa-1-azabicyclo[3,2,0] heptan-7-one-3-yl)methyl-oxycarbonyl, a $C_{2-17}$ alkenyl group which may be substituted by carboxy group or (3RS, 5SR)-(4oxa-1-azabicyclo[3,2,0] heptan-7-one-3-yl)methyloxycarbonyl, a $C_{2-4}$ alkynyl group, a $C_{3-6}$ cycloalkyl group which may be substituted by carboxy group or phenyl group which may have 1, 2 or 3 substituents selected from the group consisting of cyano group, halogen atom, carboxy group, $C_{1-6}$ alkoxy group which may be substituted by carboxy group, $C_{1-6}$ alkyl group, amino group or hydroxy group.

—$OR_2$ wherein $R_2$ is a hydrogen atom or benzyl group which may be substituted by 1 or 2 $C_{1-6}$ alkoxy group.

—$S(O)_nR_3$ wherein $R_3$ is phenyl group or a benzyl group which may be substituted by $C_{1-6}$ alkyl group, n is 0, 1 or 2; or —$CH_2OH$ Examples of $C_{1-9}$ alkyl group as the substituents in $R_1$ are straight- or branched-chain alkyl groups having 1 to 9 carbon atoms such as methyl, ethyl, propyl, pentyl, hexyl, heptyl, octyl, nonyl, 2-methylpropyl, 3-methylbutyl, 4-methylpentyl, 5-methylhexyl, 6-methylheptyl, 7-methyloctyl, 1-methylpropyl, 1-methylbutyl, 1-methylpentyl, 1-methylhexyl, 1-methylheptyl, 1-methyloctyl and the like.

Examples of halogen atom as substituents in $R_1$ are fluorine, chlorine, bromine or iodine atom.

Examples of $C_{2-17}$ alkenyl group as the substituents in $R_1$ are straight- or branched-chain alkenyl group having 2 to 17 carbon atoms such as ethenyl, 1-propenyl, 2-propenyl, 1-butenyl, 2-butenyl, 1,3-butadienyl, 1-pentenyl, 1,3-pentadienyl, 1-heptenyl, 1,3-heptadienyl, 1,3,5-heptatrienyl, 1-decenyl, 1,3-decadienyl, 1,3,5-decatrienyl, 1-pentadecenyl, 1,3-pentadecadienyl, 1,3,5-pentadecatrienyl, 1-heptadecenyl, 1,3-heptadecadienyl, 1,3,5-heptadecatrienyl, 8,11,14-heptadecatrienyl and the like.

Examples of $C_{2-4}$ alkynyl group as the substituents in $R_1$ are ethynyl, 1-propynyl, 2-propynyl, 1-butynyl, 2-butynyl, 3-butynyl and the like.

Examples of $C_{3-6}$ cycloalkyl group as the substituent in $R_1$ are cyclopropyl, cyclobutyl, cyclopenyl, cyclohexyl and the like.

Examples of $C_{1-6}$ alkoxy group as the substituent in $R_1$ or $R_2$ are straight- or branched-chain alkoxy groups having 1 to 6 carbon atoms such as methoxy, ethoxy, propoxy, 1-methyl ethoxy, butoxy, 2-methylpropoxy, pentyloxy, 3-methylbutoxy, 1,1-dimethylethoxy, hexyloxy, 4-methylpentyloxy and the like.

More specifically, R, in general formula (I), is:

—OCORR$_1$ wherein R$_1$ is selected from hydrogen, methyl, propyl, pentyl, hexyl, heptyl, 1-methylethyl, 2-methylpropyl, 3-methylbutyl, 1-methylbutyl, chloromethyl, 2-carboxyethyl, 1-hydroxy-2-[(3RS,5SR)-(4-oxa-1-azabicyclo [3,2,0]heptan-7-one-3-yl)methyloxycarbonyl]ethyl, 1,2-dihydroxy-2-[(3RS,5SR)-(4-oxa-1-azabicyclo[3,2,0] heptan-7-one- 3-yl)methyloxycarbonyl]ethyl, 1,3-pentadienyl, 8,11,14-heptadecatrienyl, 2-carboxyethenyl, 2-[(3RS, 5SR)-(4-oxa-1-azabicyclo[3,2,0]heptan-7-one-3yl)methyloxycarbonyl]ethenyl, ethynyl, 3-butynyl, phenyl, 2,4,6-trimethylphenyl, 4-methoxyphenyl, 4-hyroxyphenyl, 3,4-dihydroxyphenyl, 2-carboxyphenyl, 4-(carboxymethyloxy)phenyl, 4-fluorophenyl, 2,4,5-trifluorophenyl, 4-cyanophenyl, 4-aminophenyl, 4-hydroxy-3,5-dimethoxyphenyl or 2-carboxycyclohexyl.

—OR$_2$ wherein R$_2$ is selected from hydrogen, 4-methoxybenzyl or 3,4-dimethoxybenzyl group.

—S(O)$_n$R$_3$ wherein R$_3$ is phenyl group or a benzyl group which may be substituted by C$_{1-3}$ alkyl group, n is 0, 1 or 2.

or —CH$_2$OH

Examples of pharmaceutically acceptable salts are sodium, potassium, calcium, magnesium or hydrochloride.

The present invention provides a method of treating tumor in mammalian animals which comprises administering to a mammalian animals having tumor with an effective amount of the derivatives of formula (I).

Furthermore, the present invention provides use of the derivatives of formula (I) for the preparation of a pharmacological composition for treatment of tumor.

The bicyclic nucleus carries two asymmetric carbon atoms at position 3 and 5 and can exist as 4-diastereoisomers. In general the preferred isomer is that in which the hydrogen atoms at C$_3$ and C$_5$ are trans to each other for superior toxicity against different malignant cell lines such as P388 (derived from mouse leukemia), NUGC4 (derived from human gastric cancer), WI38 (derived from human lung fibroblastoma), L-1210, Sarcoma180, colon26. Such diastereoisomers and their mixtures are also included within the use of the oxapenam derivatives as antitumor agents.

Antitumor activity of compounds described above is expected against some solid cancers such as stomach, lung, breast, lever, uterus, leukemia and so on.

DESCRIPTION OF THE PREFERRED EMBODIMENT

The present invention relates to the use of oxapenam derivatives having excellent antitumor activity. The compounds of this invention are characterized by having

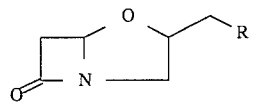
(I)

an alkanoyloxymethyl, thiomethyl or alkoxymethyl group on position-3 or 4-oxa-1-azabicyclo [3,2,0] heptan-7-one ring skeleton. The 3-alkanoyloxymethyl and thiomethyl derivatives were prepared by a general synthetic scheme as represented below (J. Chem. Soc. Perkin Trans. I, 2222, 1980).

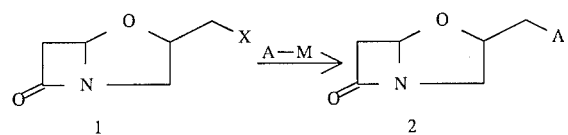

Wherein X is a good leaving group and A is a nucleophile. Suitably X is a halogen atom selected from chlorine, bromine or iodine. A is an alkanoyloxy or arylthio group. M is a sodium or potassium metal.

The preparation of compound 1 was carried out by the synthetic route as described in J. Chem. Soc. Perkin Trans. I, 2222, 1980, starting from 4-acetoxyazetidinone.

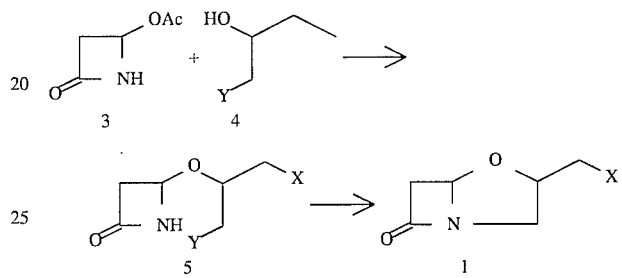

Wherein X is defined as above and Y is a leaving group selected from a chlorine, bromine, iodine or methanesulphonyloxy group.

A further suitable transformation of compound I when R is S-R$_3$, by the oxidation of a thio group with a suitable oxidizing agent, such as m-chloroperbenzoic acid, peracetic acid or hydrogen peroxide to SOR$_3$ and SO$_2$R$_3$, has been done as shown below (British Patent 1515241).

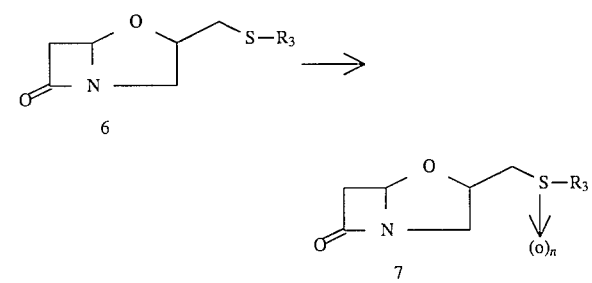

Wherein n=1 or 2 and R$_3$ is the same as defined above.

The preparation of compound 10 was done by the synthetic scheme as shown below.

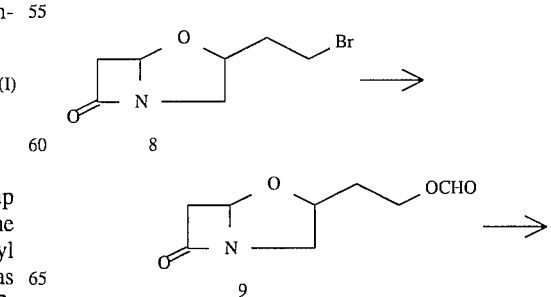

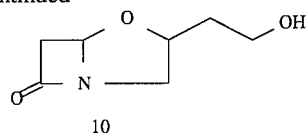

Compound 8 was prepared according to the literature procedure (British Patent 1515241) and was converted to hydroxyethyl clavam 10 [Tetrahedron, 2467–2474 (1987)] via the formyloxy ethyl clavam 9 followed by base (NaHCO₃) hydrolysis.

The preparation of the compounds of formula 13 was done by the known synthetic scheme as shown below [Tetrahedron, 2467–2474 (1987)].

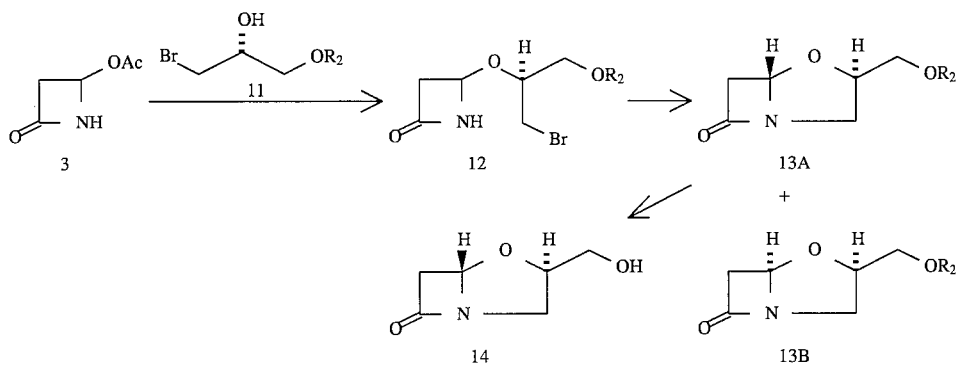
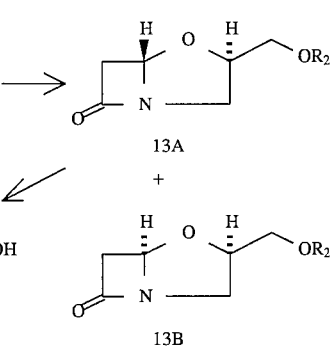

The chiral intermediate 11 was prepared from the commercially available glycerol derivative 15 according to the known route as follows.

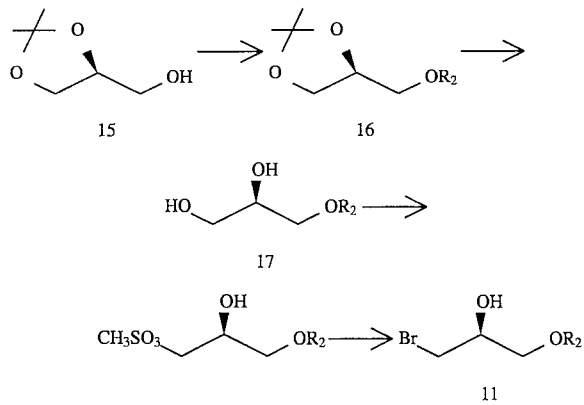

Wherein $R_2$ is a suitable protective group which can be removed under mild oxidative conditions such as 4-methoxybenzyl or 3,4-dimethoxybenzyl. Conversion of compound 12 to 13 ($R_2$=4-methoxybenzyl or 3,4-dimethoxybenzyl) was done by using a suitable base such as potassium carbonate, sodium carbonate, cesium carbonate in a non reactive solvent such as dimethylformamide, dimethylsulfoxide, hexamethylphosphoric triamide. At this stage, two stereoisomers 13A and 13B were separated by column chromatography. Removal of a protective group was achieved by suitable oxidant such as ammonium cerium (IV) nitrate or 2,3-dichloro-5,6-dicyano-1,4-benzoquinone (DDQ).

The compound of the invention, when used as an agent for treating malignant tumors of mammals including humans, may take pharmaceutical dosage forms including parenteral preparations such as injections, suppositories, aerosols and the like and oral preparations such as tablets, coated tablets, powders, granules, capsules, liquids and the like. Injections are generally preferred. The above preparations are formulated in a manner known in the art.

For the formulation of solid preparations for oral administration an excipient, and if desired, a binder, disintegrator, lubricant, coloring agent, corrigent, flavor, etc. are added to the compound of the invention, and then tablets, coated tablets, granules, powders, capsules or the like are prepared in a conventional manner.

For the formulation of injections, a pH adjusting agent, buffer, stabilizer, isotonic agent, local anesthetic or the like is added to the active ingredient of the invention, and injections for subcutaneous, intramuscular or intravenous administration can be prepared in a conventional manner.

For the formulation of suppositories, a base, and if desired, a surfactant are added to the active ingredient of the invention, and the suppositories are prepared in a conventional manner.

The excipients useful for the solid preparations for oral administration are those generally used in the art, and useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, schellac, sucrose, water, ethanol, propanol, carboxymethylcellulose, potassium phosphate and the like, lubricants such as magnesium stearate, talc and the like, and further include additives such as usual known coloring agent, disintegrators and the like. Examples of bases useful for the formulation of suppositories are, for example, oleaginous bases such as cacao butter, polyethylene glycol, lanolin, fatty acid triglycerides, Witepsol (trademark, Dynamite Nobel Co., Ltd.) and the like. Liquid preparations may be in the form of aqueous or oleaginous suspension, solution, syrup, elixir and the like, which can be prepared by a conventional way using usual additives.

The amount of the compound (I) of the invention to be incorporated into the pharmaceutical composition of the invention varies with the dosage form, solubility and chemical properties of the compound, administration route, administration scheme and the like. Preferably the amount is about 1 to 25 w/w % in the case of oral preparations, and about 0.1 to about 5 w/w % in the case of injections which are parenteral preparations.

The dosage of the compound (I) of the invention is suitably determined depending on the individual cases taking symptoms, age and sex of the subject and the like into consideration. Usually, the dosage in the case of oral administration is about 50 to about 1000 mg per day for an adult in 2 to 4 divided doses, and the dosage in the case of injection, for example, by intravenous administration is 2 ml (about 1 to about 50 mg) which is administered once a day for an adult wherein the injection ay be diluted with physiological saline or glucose injection liquid if so desired, and slowly administered over at least 5 minutes. The dosage in the case of suppositories is about 1 to about 500 mg which is administered once or twice a day at an interval of 6 to 12 hours wherein the suppositories are administered by insertion into the rectum.

Given below are Preparation Examples. In the Preparation Examples that follow, the compound numbers correspond to the compound numbers used in the Examples to be described later.

Preparation Example 1: Tablets

| Compound 31 | 50 g |
|---|---|
| Lactose | 200 g |
| Corn starch | 80 g |
| Hydrolyzed starch | 20 g |
| Potassium stearate | 10 g |
| | 360 g |

Compound 31, lactose, corn starch and hydrolyzed starch were mixed, and granulated by adding water to prepare an active paste. After drying overnight at 45° C., the granules were sieved. Potassium stearate was added thereto and the tablets weighing 360 mg and having a diameter of 10 mm were produced by means of tabletting machine.

Preparation Example 2: Capsules

| Compound 42 | 25.0 g |
|---|---|
| Lactose | 150.0 g |
| Corn starch | 40.0 g |
| Talc | 5.0 g |
| Per capsule | 200.0 mg |

Compound 42, lactose and corn starch were mixed and pulverized. After addition of talc, the mixture was placed into hard gelatin capsules.

Preparation Example 3: Injections

To Compound 40 (50 g) and 400 g of glucose was added distilled water for injection with stirring until the total volume became 10 liters. The mixture was filtered for sterilization and placed into ampoules, and nitrogen gas was aerated therein followed by sealing, thereby producing injection preparations each having a volume of 10 ml per ampoule.

Preparation Example 4: Suppository Form

"Witepsol W-35" (trademark, product of Dynamite Nobel Co., Ltd., West Germany) was fused at about 60° C. and the solution was maintained at about 45° C. The solution and the compound 6 was mixed in the following proportions and shaped into a suppository form weighing 1 g each with use of a suitable suppository-forming device.

| Components | mg/suppository |
|---|---|
| Compound 6 | 400.0 |
| Witepsol W-35 | 600.0 |
| | 1,000.0 |

The compounds of general formula (I), required for the use as antitumor activity, were prepared by the procedure either as described in literature or within the skill of art. The compounds which have been used in this invention as antitumor agents, are reported as reference examples.

REFERENCE EXAMPLE 1

4-(1,3-Dibromoisopropoxy)azetidinone

A mixture of 4-Acetoxyazetidinone (6.0 g), 1,3-Dibromo-2-propanol (6.5 g), Triethylamine (6.5 ml), Palladium acetate (0.6 g) and dry Benzene (200 ml) was stirred at room temperature under Nitrogen for 24 hrs. After the reaction, resulting precipitate was filtered off by using celite. The filtrate was washed with water, brine, and dried over Sodium sulfate. The residual oil after evaporation was purified by column chromatography using Hexane and Ethyl acetate (4:1) as eluent. Yield: 5.58 g (64.8%), m.p. 80.0°–82.0° C. $^1$H NMR (CDCl$_3$): 2.92–3.27 (2H, m), 3.43–3.60 (4H, m), 3.86–3.97 (1H, m), 5.27 (1H, dd, J=1.4, 3.7), 6.40 (1H, br, s). IR (Nujol), cm$^{-1}$: 3270, 1766.

REFERENCE EXAMPLE 2

3-Bromomethyl-4-oxa-1-azabicyclo[3,2,0]heptan-7-one

A mixture of 4-(1,3-Dibromo-2-propoxy) azetidinone (13.4 g), Cesium carbonate (18.3 g) and Dimethyl sulfoxide (200 ml) was stirred at room temperature for 4 hrs. The reaction mixture was extracted with Ethyl acetate, washed with water, brine and dried over Sodium sulfate. The ethyl acetate extract was concentrated and the residue was purified by silicagel column chromatography using Hexane and Ethyl acetate (5:1) as eluent. Two isomers were isolated. (3RS, 5SR)-3-Bromomethyl-4-oxa-1-azabicyclo[3,2,0]heptan-7-one; Yield: 5.48 g (56.9%). NMR (CDCl$_3$):2.83–3.30 (1H, m), 3.47 (2H, d, J=5.2), 4.07 (1H, dd, J=6.7, 11.9), 4.52–4.64 (1H, m), 5.44 (1H, d, J=2.7). IR (Neat), cm$^{-1}$: 2945, 1766. (3RS, 5RS)-3-Bromomethyl-4-oxa-4-azabicyclo[3,2,0]heptan-7-one: Yield: 1.20 g (12.5%), m.p. 49°–50° C. NMR (CDCl$_3$): 2.88–3.36 (3H, m), 3.39–3.51 (2H, m), 3.27 (1H, dd, J=5.6, 11.4), 4.54–4.66 (1H, m), 5.28 (1H, d, J=2.6). IR (Nujol), cm$^{-1}$: 2908, 1766.

REFERENCE EXAMPLE 3

(3RS, 5SR)-3-Formyloxymethyl-4-oxa-1-azabicyclo[3,2,0]-heptan-7-one (R=OCHO)

A mixture of reference example 2 (719 mg), Sodium formate (475 mg) and Hexamethylphosphoric triamide (3 ml) was stirred at 70° C. for 28 hrs. The reaction mixture was diluted with Ethyl acetate, washed with water, brine, and dried over Sodium sulfate. The title compound was obtained after column purification of residue using Hexane and Ethyl acetate (2:1) as eluent. Yield: 267 mg (45%). NMR (CDCl$_3$): 2.83 (1H, dd J=5.6, 11.6), 2.87 (1H, d, J=16.7), 3.31 (1H, dd, J=15.8), 4.01 (1H, dd, J=7.1, 11.7), 4.19–4.35 (2H, m), 4.53–4.64 (1H, m), 5.37 (1H, d, J=2.7), 8.11 (1H, s). IR (Neat), cm$^{-1}$: 2945, 1773, 1714.

By using the procedure described above the reference examples 4–20, 31–35 were prepared and their spectroscopic date are given below.

REFERENCE EXAMPLE 4

(3RS, 5SR)-3-Acetoxymethyl-4-oxa-1-azabicyclo[3,2,0]-heptan-7-one (R=OCOCH$_3$)

Yield: 360 mg (65%). NMR (CDCl$_3$): 2.11 (1H, s), 2.79 (1H, dd, J=6.4, 11.7), 2.87 (1H, d, J=16.2), 3.31 (1H, dd, J=2.8, 16.2), 4.00 (1H, dd, J=6.9, 11.6), 4.09–2.24 (1H, m), 4.50, 4.62 (1H, m), 5.35 (1H, d, J=2.7). IR (Neat), cm$^{-1}$: 2960, 1781, 1738.

REFERENCE EXAMPLE 5

(3RS, 5SR)-3-Butyryloxymethyl-4-oxa-1-azabicyclo [3,2,0]heptan-7-one (R=OCO(CH$_2$)$_2$CH$_3$)

Yield: 209 mg (49%). NMR (CDCl$_3$): 0.96 (3H, t, J=7.3), 1.67 (2H, sext, J=7.4), 2.34 (2H, t, J=7.3), 2.80 (1H, dd, J=6.7, 11.2), 2.86 (1H, d, J=16.4), 3.30 (1H, dd, J=2.9, 16.1), 3.99 (1H, dd, J=6.8, 11.6), 4.10–4.25 (2H, m), 4.51–4.62 (1H, m), 5.35 (1H, d, J=2.7). IR (Neat), cm$^{-1}$: 2940, 1776, 1728.

REFERENCE EXAMPLE 6

(3RS, 5SR)-3-Hexanoyloxymethyl-4-oxa-1-azabicyclo-[3,2,0]heptan-7-one (R=OCO(CH$_2$)$_4$CH$_3$)

Yield: 154 mg (64%). NMR (CDCl$_3$): 0.87–0.93 (3H, m), 1.27–1.38 (4H, m), 1.57–1.71 (2H, m), 2.36 (2H, t, J=7.4), 2.75–3.35 (3H, m), 3.99 (1H, dd, J=6.8, 11.5), 4.10–4.25 (2H, m), 4.51–4.62 (1H, m), 5.35 (1H, d, J=2.6). IR (Neat), cm$^{-1}$: 2930, 1779, 1730.

REFERENCE EXAMPLE 7

(3RS, 5SR)-3-(n-Octanoyloxymethyl)-4-oxa-1-azabicyclo[3,2,0] heptan-7-one (R=OCO(CH$_2$)$_6$CH$_3$)

Yield: 225 mg (56%). NMR (CDCl$_3$): 0.88 (3H, t, J=6.7), 1.28 (7H, br, s), 1.63 (2H, t, J=7.2), 2.36 (2H, t, J=7.3), 2.80 (1H, dd, J=6.6, 11.9), 2.86 (1H, d, J=16.1), 3.30 (1H, dd, J=3.0, 15.3), 3.99 (1H, dd, J=7.1, 11.6), 4.12–4.18 (2H, m), 4.50–4.62 (1H, m), 5.35 (1H, d, J=2.6). IR (Neat), cm$^{-1}$: 2920, 1779, 1730.

REFERENCE EXAMPLE 8

(3RS, 5SR)-3-Decanoyloxymethyl-4-oxa-1-azabicyclo-[3,2,0]heptan-7-one (R=OCO(CH$_2$)$_8$CH$_3$)

Yield: 195 mg (66%). NMR (CDCl$_3$): 0.88 (3H, br, t, J=6.6), 1.27 (12H, br, s), 1.63 (2H, br, t, J=7.1), 2.35 (2H, t, J=7.7), 2.79 (1H, dd, J=6.3, 11.5), 2.86 (1H, d, J=16.5), 3.30 (1H, dd, J=2.6, 16.4), 3.99 (1H, dd, J=6.9, 11.5), 4.09–4.22 (1H, m), 4.50–4.61 (1H, m), 5.34 (1H, d, J=2.6). IR (Neat), cm$^{-1}$: 2915, 1780, 1731.

REFERENCE EXAMPLE 9

(3RS, 5SR)-3-(2-Methylpropionyloxymethyl)-4-oxa-1-azabicyclo [3,2,0]heptan-7-one (R=OCOCH(CH$_3$)$_2$)

Yield: 62 mg (29%). NMR (CDCl$_3$): 1.19 (6H, d, J=7.8), 2.60 (1H, quin, J=6.7), 2.81 (1H, dd, J=6.2, 10.7), 2.86 (1H, d, J=16.1), 3.30 (1H, dd, J=1.7, 14.3), 3.98 (1H, dd, J=7.2, 4.5), 4.17 (2H, d, J=4.6), 4.51–4.63 (1H, m), 5.35 (1H, d, J=2.7). IR (Neat), cm$^{-1}$: 2950, 1770, 1728.

REFERENCE EXAMPLE 10

(3RS, 5SR)-3-Methylbutyryloxymethyl-4-oxa-1-azabicyclo [3,2,0]heptan-7-one (R=OCOCH$_2$CH(CH$_3$)$_2$)

Yield: 22 mg (14%). NMR (CDCl$_3$): 0.98 (6H, d, J=7.7), 1.96–2.42 (3H, m), 2.68–3.04 (2H, m), 3.31 (1H, dd, J=1.8, 14.2), 3.83–4.34 (3H, m), 4.57 (1H, m), 5.36 (1H, d, J=1.9), IR (Neat), cm$^{-1}$: 2940, 1778, 1729.

REFERENCE EXAMPLE 11

(3RS, 5SR)-3-Methylpentanoyloxymethyl-4-oxa-1-azabicyclo [3,2,0]heptan-7-one (R=OCO(CH$_2$)$_2$CH(CH$_3$)$_2$)

Yield: 104 mg (29%). NMR (CDCl$_3$): 0.90 (6H, d, J=5.9), 1.48–1.57 (3H, m), 2.36 (2H, t, J=8.0), 2.79 (1H, dd, J=5.9, 11.7), 2.86 (1H, d, J=16.8), 3.30 (1H, dd, J=2.2, 16.1), 3.93 (1H, dd, J=6.6, 11.0), 4.09–4.18 (2H, m), 4.50–4.62 (1H, m), 5.34 (1H, d, J=2.9). IR (Neat), cm$^{-1}$: 2935, 1779, 1730.

REFERENCE EXAMPLE 12

(3RS, 5SR)-3-Methylhexanoyloxymethyl-4-oxa-1-azabicyclo [3,2,0]heptan-7-one (R=OCOCH(CH$_3$)(CH$_2$)$_3$CH$_3$)

Yield: 131 mg (36%). NMR (CDCl$_3$): 0.89 (6, t, J=6.7), 1.17 (3H, d, J=6.7), 1.20–1.76 (5H, m), 2.48 (1H, sext, J=7.0), 2.80 (1H, dd, J=5.9, 11.5), 2.86 (1H, d, J=16.2), 3.30 (1H, dd, J=3.0, 16.1), 3.98 (1H, dd, J=7.1, 11.6), 4.18 (2H, d, J=4.5), 4.51–4.62 (1H, m), 5.35 (1H, d, J=2.6). IR (Neat), cm$^{-1}$: 2930, 1780, 1728.

REFERENCE EXAMPLE 13

(3RS, 5SR)-3-Chloroacetoxymethyl-4-oxa-1-azabicyclo-[3,2,0]heptan-7-one (R=OCOCH$_2$Cl)

Yield: 150 mg (34%). NMR (CDCl$_3$): 2.87 (1H, d, J=16.2), 2.83–2.99 (1H, m), 3.31 (1H, dd, J=17.3, 3.1), 3.47 (1H, d, J=5.7), 3.63 (1H, d, J=5.3)), 4.50–4.13 (1H, m), 4.51–4.65 (1H, m), 5.42 (1H, t, J=2.8). IR (Neat), cm$^{-1}$: 2940, 1771, 851.

REFERENCE EXAMPLE 14

(3RS, 5SR)-3-(2,4-Hexadienoyloxyymethyl)-4-oxa-1-azabicyclo [3,2,0]heptan-7-one
(R=OCOCH=CHCH=CHCH$_3$)

Yield: 64 mg (54%). NMR (CDCl$_3$): 1.87 (3H, d, J=4.7), 2.83 (1H, dd, J=11.6, 5.1), 2.86 (1H, d, J=16.2), 3.30 (1H, dd, J=2.8, 15.9), 4.00 (1H, dd, J=6.8, 11.5), 4.19–4.32 (2H, m), 5.36 (1H, m), (1H, d, J=2.5), 5.86 (1H, d, J=15.3), 6.11–6.29 (2H, m), 7.22–7.35 (1H, m). IR (Neat), cm$^{-1}$: 2940, 1776, 1704, 1635.

REFERENCE EXAMPLE 15

(3RS, 5SR)-3-(9, 12, 15-Octadecatrienoyloxymethyl)-4-oxa-1-azabicyclo [3,2,0]heptan-7-one
(R=OCO(CH$_2$)$_7$CH=CHCH$_2$CH=CHCH$_2$CH=CHCH$_2$CH$_3$)

Yield: 149 mg (37%). NMR (CDCl$_3$): 0.98 (3H, t, J=7.5), 1.31 (8H, br, s), 1.63 (2H, br, t, J=6.8), 2.01–2.18 (4H, m), 2.35 (2H, t, 7.4), 2.79 (1H, dd, J=6.3, 11.2), 2.86 (1H, d, J=18.7), 3.30 (1H, dd, J=2.6, 16.5), 3.99 (1H, dd, J=6.9, 11.6), 4.09–4.22 (2H, m), 4.51–4.62 (1H, m), 5.25–5.46 (7H, m). IR (Neat), cm$^{-1}$: 2915, 1781, 1731.

REFERENCE EXAMPLE 16

(3RS, 5SR)-3-Propynoyloxymethyl-4-oxa-1-azabicyclo-[3,2,0]heptan-7-one (R=OCOC≡CH)

Yield: 96 mg (49%). NMR (CDCl$_3$): 2.79–2.91 (2H, m), 2.96 (1H, s), 3.36 (1H, dd, J=2.8, 16.1), 4.02 (1H, dd, J=6.9, 11.7), 4.20 (1H, m), 4.53–4.65 (1H, m), 5.37 (1H, d, J=2.7). IR (Neat), cm$^{-1}$: 3235, 2945, 2100, 1773, 1709.

REFERENCE EXAMPLE 17

(3RS, 5SR)-3-(4-Pentynoyloxymethyl)-4-oxa-1-azabicyclo [3,2,0]heptan-7-one (R=OCO(CH$_2$)$_2$C≡CH)

Yield: 223 mg (77%). NMR (CDCl$_3$): 1.99 (6H, t, J=2.2), 2.47–2.66 (4H, m), 2.82 (1H, dd, J=6.5, 11.6), 2.86 (1H, d, J=16.2), 3.30 (1H, dd, J=2.3, 13.7), 3.99 (1H, dd, J=6.9, 4.8), 4.21 (2H, m), 4.56 (1H, m), 5.35 (1H, d, J=2.7). IR (Neat), cm$^{-1}$: 1773, 1770, 2945, 3270.

REFERENCE EXAMPLE 18

(3RS, 5SR)-3-Benzoyloxymethyl-4-oxa-1-azabicyclo-[3,2,0]heptan-7-one (R=OCCC$_6$H$_5$)

Yield: 289 mg (80%). NMR (CDCl$_3$): 2.88 (1H, d, J=16.5), 2.95 (1H, dd, J=5.3, 12.1), 3.32 (1H, dd, J=2.0, 16.5), 4.06 (1H, dd, J=7.1, 11.5), 4.24–4.77 (2H, m), 4.66–4.77 (1H, m), 5.41 (1H, d, J=2.6), 7.42–8.08 (5H, m). IR (Neat), cm$^{-1}$: 2960, 1782, 1719, 710.

REFERENCE EXAMPLE 19

(3RS, 5SR)-3-(2,4,6-Trimethylbenzoyloxymethyl-4-oxa-1-azabicyclo[3,2,0]heptan-7-one
(R=OCO—C$_6$H$_2$(CH$_3$)$_3$)

Yield: 905 mg (65%). NMR (CDCl$_3$): 2.29 (3H, s), 2.30 (6H, s), 2.85 (1H, d, J=16.3), 2.87 (1H, dd, J=5.8, 11.7), 3.29 (1H, dd, J=2.8, 15.9), 4.02 (1H, dd, J=6.8, 11.6), 4.40 (2H, d, J=5.0), 4.60–4.71 (1H, m), 5.34 (1H, d, J=2.7), 6.86 (2H, s). IR (Neat), cm$^{-1}$: 1777, 1717, 1262.

REFERENCE EXAMPLE 20

(3RS, 5SR)-3-(4-Methoxybenzoyloxymethyl-4-oxa-1-azabicyclo [3,2,0]heptan-7-one
(R=OCOC$_6$H$_4$OCH$_3$)

Yield: 241 mg (62%). m.p. 87.5°–89.0° C. NMR (CDCl$_3$): 2.88 (1H, d, J=16.8), 2.94 (1H, dd, J=5.0, 11.8), 3.31 (1H, dd, J=3.0, 15.8), 3.87 (3H, s), 4.05 (1H, dd, J=6.8, 11.4), 4.31–4.48 (2H, m), 4.65–4.76 (1H, m), 5.40 (1H, d, J=2.7), 6.90–6.97 (2H, m), 7.96–8.03 (2H, m). IR (Nujol), cm$^{-1}$: 1776, 1704, 1598.

REFERENCE EXAMPLE 21

(3RS, 5SR)-3-(4-Hydroxybenzoyloxymethyl-4-oxa-1-azabicyclo [3,2,0]heptan-7-one (R=OCOC$_6$H$_4$OH):

A mixture of 0.5 g (2.4 mmole) of reference example 2, 1.2 g (4.8 mmole) of 4-(t-Butyldimethylsilyloxy)benzoic acid and 0.48 g (4.8 mmole) Triethylamine in 15 ml of DMSO was heated at 70° for 5 hours. The reaction mixture was diluted with water and extracted with Ethyl acetate. The ethyl acetate extract was washed with water and brine solution, dried over Sodium sulphate and concentrated. The residue was dissolved in a mixture of THF (5 ml) and CH$_3$COOH (0.1 ml) and to this solution, 1N-Tetrabutylammonium fluoride in THF (3 ml) was added under stirring at room temperature. The reaction mixture was stirred for 30 minutes and filtered through silica gel. The filtrate was concentrated and the residue was purified by using flash chromatography and 40% Ethyl acetate in Hexane as eluant. Yield 160 mg (23%), m.p. 115.5°–118° C.

NMR (CDCl$_3$): 2.80–3.00 (2H, m), 3.26–3.35 (m, 1H), 3.98–4.20 (1H, m), 4.30–4.40 (2H, m), 4.64–4.78 (1H, m), 5.40 (1H, d, J=2.8 Hz), 6.84–6.94 (2H, m), 7.87–7.97 (2H, m).

REFERENCE EXAMPLE 22

(3RS, 5SR)-3-(3,4-Dihydroxybenzoyloxymethyl-4-oxa-1-azabicyclo [3,2,0]heptan-7-one
(R=OCOC$_6$H$_3$(OH)$_2$)

A mixture of 0.5 g (2.4 mmole) of reference example 2, 1.9 g (5 mmole) of 3,4-Di(t-butyldimethylsilyloxy)benzoic acid and 1.2 g (3.7 mmole) of Cesium carbonate in 15 ml of DMSO was heated at 45° C. for 3 hrs. The reaction mixture was worked up according to reference example 21 and the residue was purified by flash chromatography using 25% Ethyl acetate in Hexane as eluant. The pure product (250 mg) was dissolved in a mixture of THF (8 ml) and CH$_3$COOH (0.1 ml). 1N-Tetra-butylammonium fluoride (0.7 ml) in THF was added to above solution under stirring at room temperature. The resulting mixture was stirred for 10 minutes and purified by flash chromatography using 50% Ethyl acetate in Hexane. Yield 50 mg (7.5%).

NMR (CDCl$_3$): 2.84–2.98 (2H, m), 3.31 (1H, m), 4.00–4.18 (1H, m), 4.35–4.41 (2H, m), 4.64–4.76 (1H, m), 5.40 (1H, d, J=2.8, Hz), 5.97 (1H, s), 6.16 (1H, s), 6.92 (1H, d, J=8.8 Hz), 7.55–7.58 (2H, m).

REFERENCE EXAMPLE 23

Sodium (3RS, 5SR)-4-(4-oxa-1-azabicyclo [3,2,0]heptan-7-one-3-methyloxycarbonyl)phenoxyacetate (R=OCOC$_6$H$_4$OCH$_2$CO$_2$Na)

A mixture of reference example 22 (75 mg; 28 mmole), Allyl chloroacetate (57 mg, 0.43 mmole) and K$_2$CO$_3$ (118 mg, 0.86 mmole) in DMF (5 ml) was stirred at room temperature for 2 hrs. The reaction mixture was diluted with water and extracted with Ethyl acetate. The Ethyl acetate extract was washed with water and brine solution dried over Na$_2$SO$_4$ and concentrated. The residue was purified over silica gel using Ethyl acetate:Hexane (1:1) as eluant. Yield 80 mg (80%). The pure produce (80 mg, 0.22 mmole) was dissolved in Ethyl acetate:Dichloromethane (1:1) mixture and to this solution, Triphenylphosphine (5 mg, 0.019 mmole), Sodium 2-ethylhexanoate (0.11 ml, 0.22 mmole) and Tetrakis triphenylphosphine palladium(0) (8 mg, 0.0073 mmole) was added. The mixture was stirred at room temperature for 10 minutes. Separated solid was filtered, washed with Ethyl acetate and Ether, dried under vacuum. Yield 40 mg (53%) m.p. 190°–200° C.

NMR (DMSO-d$_6$): 2.78–2.93 (2H, m), 3.35–3.41 (1H, m), 3.87–3.95 (1H, dd, J=7.1, 11.5 Hz), 4.20 (2H, s), 4.32–4.34 (2H, m), 4.65–4.77 (1H dd, J=5.37 (1H, d, J=2.5 Hz), 6.90 (1H, d, J=4.4 Hz), 7.85 (1H, d, J=8.9 Hz).

REFERENCE EXAMPLE 24

Sodium (3RS, 5SR)-2-(4-oxa-1-azabicyclo [3,2,0]heptan-7-one-3-methyloxycarbonyl)cyclohexyl-2-carboxylate (R=OCOC$_6$H$_{10}$COONa):

A mixture of reference example 2 (0.3 g; 1.4 mmole), 2-Allyloxycarbonyl)cyclohexanecarboxylic acid (0.62 g, 2.9 mmole) and Cesium carbonate (0.71 g, 2.2 mmole) in HMPA (5 ml) was heated at 55° C. for 4 hrs. The reaction mixture was worked up as described above and purified by column chromatographed on silica gel using 25% Ethyl acetate in Hexane as eluant. Yield 400 mg (82%). The allyl ester of pure product was hydrolysed by the procedure as described in reference example 23 except the stirring time for 2 hrs. Yield 55 mg (29%), m.p. >200° C. (dec).

NMR (DMSO-d$_6$): 1.00–1.30 (4H, m), 1.40–1.76 (3H, m), 1.85–3.10 (1H, m, 2.16–2.58 (2H, m), 2.6–2.90 (2H, m), 3.18–3.34 (1H, d, J=16.0 Hz) 3.62–3.78 (1H, m), 3.82–4.00 (2H, m) 4.36–4.52 (1H, m), 5.24 (1H, s).

REFERENCE EXAMPLE 25

Sodium (3RS, 5SR)-2-[(4-oxa-1-azabicyclo [3,2,0]heptan-7-one-3-yl)methyloxycarbonyl]benzoate (R=OCO—C$_6$H$_4$—CO$_2$Na)

A mixture of reference example 2 (0.46 g; 2.23 mmole), 2-Allyloxycarbonyl benzoic acid (0.9 g, 4.46 mmole) and Triethylamine (0.44 g, 4.46 mmole) in DMSO (5 ml) was heated at 70° C. for 15 hrs. The reaction mixture was worked up as usual and the residue was purified on silica gel using Ethyl acetate:Hexane (1:2) as eluant. Yield 450 mg (62%). The allyl ester was deprotected by using the procedure as described in reference example 23, which gave the title product as sodium salt. Yield 310 mg (76%), m.p. 190°–194° C.:

NMR (DMSO-d$_6$): 2.77 (1H, d, J=16.2 Hz), 2.92–3.01 (1H, dd, J=6.0 and 11.4 Hz), 3.26–3.33 (1H, m), 3.81–3.91 (1H, dd, J=7.0 and 11.5 Hz), 4.21 (2H, d, J=4.4 Hz), 4.56–4.67 (1H, m), 5.30 (1H, d, J=2.5 Hz) 7.21–7.37 (3H, m), 7.67 (1H, d, J=6.4 Hz).

REFERENCE EXAMPLE 26

Sodium [(3RS, 5R)-4-oxa-1-azabicycle[3,2,0]heptan-7-one-3-yl)methyl]succinate (R=OCOCH$_2$CH$_2$COONa)

A mixture of reference example 2 (0.33 g; 1.6 mmole), Allyl hydrogen succinate (0.5 g, 3.2 mmol) and Cesium carbonate (0.78 g, 2.4 mmol) in HMPA (5 ml) was heated at 50° C. for 5 hrs. The reaction mixture was worked up as usual and purified over silica gel using Ethyl acetate in Hexane as gradient eluant to give the pure allyl ester of title product in 69% yield. NMR (CDCl$_3$): 2.68 (4H, s), 2.76–2.50 (2H, m), 3.25–3.34 (1H, m), 3.93–4.03 (1H, dd, J=6.9 and 11.6 Hz), 4.18–4.22 (2H, m), 4.55–4.62 (3H, m), 5.21–5.37 (3H, m), 5.81–6.01 (1H, m).

A mixture of allyl ester (200 mg, 0.71 mmol), 26 mg (0.10 mmol) of Triphenylphosphine, 0.36 ml (0.72 mmol) of Sodium 2-ethylhexanoate and 36 mg (0.33 mmol) of Tetrakis triphenylphosphine Pd(0) in 10 ml of Ethyl acetate/ CH$_2$Cl$_2$ (1:1) was stirred at room temperature for 1 hr. The resulted solid was filtered, washed with Ethyl acetate and dried. Yield: 70 mg (37%); m.p. 140° C. (dec.); NMR (DMSO-d$_6$): 1.91–2.06 (2H, m), 2.20–2.35 (2H, m), 2.67–2.75 (2H, m), 3.21–3.29 (1H, m, 3.70–3.79 (1H, m), 3.94–4.20 (2H, m), 4.39–4.52 (1H, m), 5.25 (1H, d, J=2.5 Hz).

REFERENCE EXAMPLE 27

Sodium [(3RS, 5SR)-(4-oxa-1-azabicyclo[3,2,0]heptan-7-one-3-yl)methyl]fumarate (R=OCOCH=CH—COONa)

A mixture of reference example 2 (0.37 g; 1.2 mmole), Allyl hydrogen fumarate (0.56 g, 3.6 mmol) and Cesium carbonate (0.87 g, 2.7 mmol) in 10 ml of HMPA was heated at 45°–50° C. for 16 hrs. The reaction mixture was worked up as usual and the residue was purified by flash column chromatography using Ethyl acetate and Hexane as gradient eluant. After purification two products were obtained. allyl ester of trans isomer, Yield: 340 mg (68%), NMR (CDCl$_3$): 2.87 (1H, d, J=16.6), 2.83 (1H, dd, J=6.4, 4.4), 3.31 (1H, dd, d=2.93, 16.61), 4.01 (1H, dd, J=7.3, 11.2), 4.28–4.32 (2H, m), 4.54–4.66 (1H, m), 4.70 (2H, dd, J=1.5, 5.9), 5.26–5.40 (3H, m), 5.85–6.04 (1H, m), 6.90 (2H, s); allyl ester of cis isomer, Yield: 90 mg (18%), NMR (CDCl$_3$): 2.80–2.90 (2H, m), 3.30 (1H, dd, J=2.4, 16.6), 4.00 (1H, dd, J=6.8, 11.7), 4.21–4.38 (2H, m), 4.58–4.63 (1H, m), 4.70 (2H, dd, J=1.0, 5.9), 5.26–5.41 (3H, m), 5.85–6.02 (1H, m), 6.30 (2H, s).

The trans isomer was de-esterified by using the procedure as described in reference example 26. The reaction mixture was stirred for 5 hrs at room temperature. The title compound was separated after cooling the reaction mixture.

Yield: 53%, m.p. 130° C. (dec.); NMR (DMSO-$d_6$): 2.77–2.85 (2H, m), 3.36 (1H, dd, J=2.5, 16.3), 3.86 (1H, dd, J=7.1, 11.6), 4.19 (2H, d, J=3.6), 4.53–4.68 (1H, m), 5.32 (1H, d, J=2.4), 6.18 (1H, d, J=15.8), 6.75 (1H, d, J=15.7).

REFERENCE EXAMPLE 28

Bis [(3RS, 5SR)-(4-oxa-1-azabicyclo[3,2,0]heptan-7-one-3-yl)-methyl]-2-hydroxysuccinate (R=OCOCH(OH)CH$_2$—COOCH$_2$Clavam)

A mixture of reference example 2 (1.15 g; 5.6 mmole), and Disodium 2-hydroxysuccinate (0.5 g, 2.8 mmol) in 8 ml of HMPA was heated at 70°–50° C. for 48 hrs. The reaction mixture was diluted with water and extracted with Ethyl acetate. The extract was washed with water and brine, dried over Na$_2$SO$_4$ and concentrated. The residue was purified over silica gel using a mixture of Ethyl acetate and Hexane as gradient eluant. Yield: 160 mg (15%). NMR (CDCl3): 1.58 (2H, s), 2.78–2.91 (4H, m), 3.27–3.36 (2H, dd, J=2.5 and 16.3 Hz), 3.97–4.07 (2H, m), 4.24–4.48 (4H, m), 4.50–4.63 (4H, m), 5.35–5.38 (2H, m).

REFERENCE EXAMPLE 29

Bis [(3RS, 5SR)-(4-oxa-1-azabicyclo[3,2,0]heptan-7-one-3-yl)-methyl]-2,3-dihydroxysuccinate (R=OCOCH(OH)CH(OH)COOCH$_2$ Clavam)

A mixture of reference example 2 (1.3 g; 6.3 mmol), Disodium 2,3-dihydroxysuccinate (0.5 g, 2.6 mmol), and Potassium iodide (0.85 g, 5.1 mmol) in 10 ml of HMPA was heated at 70° C. for 24 hrs. The reaction mixture was worked up as usual and purified over silica gel using Ethyl acetate in Hexane as gradient eluant. Yield: 60 mg (6%). NMR (CDCl$_3$): 1.63 (1H, bs), 2.74–2.93 (6H, m), 3.26–3.35 (2H, dd, J=1.9 and 16.3 Hz), 3.94–4.33 (6H, m), 4.51–4.58 (3H, m), 5.34–5.36 (2H, m).

REFERENCE EXAMPLE 30

Bis [(3RS, 5SR)-(4-oxa-1-azabicyclo[3,2,0]heptan-7-one-3-yl)-methyl]maleate (R=OCOCH=CH—COOCH$_2$Clavam)

Reference example 2 and Disodium maleate was coupled by using the procedure described in reference example 28 and title compound was obtained. Yield: 58% NMR (CDCl$_3$): 2.78–2.90 (4H, m), 3.25–3.35 (2H, dd, J=2.5 and 16.2 Hz), 3.96–4.17 (2H, m), 4.27–4.30 (4H, m), 4.54–4.65 (2H, m), 5.35 (2H, d, J=2.6 Hz), 6.32 (2H, s).

REFERENCE EXAMPLE 31

(3RS, 5SR)-3-(4-Fluorobenzoyloxymethyl)-4-oxa-1-azabicyclo [3,2,0]heptan-7-one (R=OCOC$_6$H$_4$F)

Yield: 284 mg (71%). NMR (CDCl$_3$): 2.98 (1H, d, J=16.6), 2.92 (1H, dd, J=6.2, 11.6), 3.32 (1H, dd, J=2.8, 16.1), 4.06 (1H, dd, J=7.1, 11.6), 4.34–4.50 (2H, m), 4.65–4.76 (1H, m), 5.40 (1H, d, J=2.6), 7.09–7.18 (2H, m), 8.03–8.10 (2H, m). IR (Neat), cm$^{-1}$: 2945, 1778, 1714, 1594.

REFERENCE EXAMPLE 32

(3RS, 5SR)-3-(2,4,5-Trifluorobenzoyloxymethyl)-4-oxa-1-azabicyclo[3,2,0]heptan-7-one (R=OCOC$_6$H$_2$F$_3$))

Yield: 74 mg (18%). m.p. 58.5°–60° C. NMR (CDCl$_3$): 2.19 (1H, s), 2.93 (2H, m), 3.33 (1H, dd, J=13.5, 2.4), 4.09 (1H, dd, J=9.6, 6.5), 4.40 (2H, m), 4.71 (1H, m), 5.42 (1H, d, J=2.4), 7.05 (1H, m), 7.83 (1H, m), IR (Nujol), cm$^{-1}$: 1777, 1716, 1615.

REFERENCE EXAMPLE 33

(3RS, 5SR)-3-(4-Cyanobenzoyloxyymethyl)-4-oxa-1-azabicyclo [3,2,0]heptan-7-one (R=OCOC$_6$H$_4$CN)

Yield: 210 mg (48%). m.p. 101.6°–102.6° C. NMR (CDCl$_3$): 2.11 (1H, s), 2.90 (1H, d, J=15.9), 2.94 (1H, t, J=6.3), 3.32 (1H, dd, J=13.3, 2.9), 4.11 (1H, m), 4.46 (2H, m), 4.72 (1H, m), 5.39 (1H, d, J=2.7), 7.77 (2H, d, J=8.1), 8.15 (2H, d, J=8.3). IR (Nujol), cm$^{-1}$: 1766, 1709, 2333.

REFERENCE EXAMPLE 34

(3RS, 5SR)-3-(4-Aminobenzoyloxymethyl)-4-oxa-1-azabicyclo [3,2,0]heptan-7-one (R=OCOC$_6$H$_4$NH$_2$)

Yield: 146 mg (33%). m.p. 132.6°–134.5° C. NMR (CDCl$_3$): 1.58 (2H, s), 2.92 (2H, m), 3.30 (1H, dd, J=2.9, 13.1), 3.99–4.17 (3H, m), 4.28–4.45 (2H, m), 4.69 (1H, m), 5.39 (1H, d, J=2.6), 6.64 (2H, m), 7.83 (2H, m). IR (Nujol), cm$^{-1}$: 3400, 1761, 1671.

REFERENCE EXAMPLE 35

(3RS, 5SR)-3-(4-Hydroxy-3,5-dimethoxybenzoyloxymethyl)-4-oxa-1-azabicyclo [3,2,0]heptan-7-one (R=OCOC$_6$H$_2$OH(OCH$_3$)$_2$)

Yield: 88 mg (18%). NMR (CDCl$_3$): 2.89 (1H, d, J=16.1), 2.93 (1H, dd, J=5.9, 10.2), 3.31 (1H, dd, J=1.5, 15.4), 3.95 (6H, s), 4.07 (1H, dd, J=7.3, 11.7), 4.412 (2H, d, J=3.7), 4.66–4.77 (1H, m), 5.41 (1H, d, J=2.2), 5.95 (1H, s), 7.32 (2H, s). IR (Neat), cm$^{-1}$: 3395, 2905, 1765, 1703.

REFERENCE EXAMPLE 36

(R)-3-(3,4-Dimethoxybenzyloxy)-1,2-propandiol (compound17, R$_2$=OCH$_2$C$_6$H$_3$(OCH$_3$)$_2$)

To the suspension of Sodium hydride (60% oil dispersion, 4.85 g) in dry Dimethyl sulfoxide (100 ml), solution of (R)-(−)-2,2-Dimethyl-1,3-dioxolane-4-methanol (10.68 g) in dry Tetrahydrofuran (30 ml) was added dropwise under Nitrogen atmosphere at room temperature. After evolution of Hydrogen stopped, solution of 3.4-Dimethoxybenzyl chloride (16.42 g) in dry Dimethyl sulfoxide (30 ml) was added dropwise under the same condition. After 10 hrs of stirring, the reaction mixture was diluted with Diethyl ether, washed with water, followed by brine and then dried over Magnesium sulfate, then 1N-Hydrochloric acid (50 ml) and Tetrahydrofuran (100 ml) was added to the residue and stirred for 6 hrs. The reaction mixture was neutralized with Sodium hydrogen carbonate, extracted with Chloroform and dried over Magnesium sulfate. The title compound was obtained after column purification (Hexane+Ethyl acetate 1:2~Ethyl acetate+Acetone (10:1) as oil. Yield: 18.31 g (94%). NMR (CDCl$_3$): 2.16 (1H, br, s), 3.55 (2H, m), 3.67 (2H, m), 3.88 (3H, s), 3.89 (3H, s), 3.92 (1H, m), 4.49 (2H, s). IR (Neat), cm$^{-1}$: 3385, 2910, 1505. [α]$^{25}_D$=+1.0° (C=2.0, Chloroform).

REFERENCE EXAMPLE 37

(S)-1-Bromo-3-(3,4-dimethoxybenzyloxy)-2-propanol (compound11, R$_2$=OCH$_2$C$_6$H$_3$(OCH$_3$)$_2$)

To a solution of reference example 36 (14.98 g) and Pyridine (9.78 g) in dry Dichloromethane (200 ml), solution of Methanesulfonyl chloride (14.17 g) in dry Dichloromethane (50 ml) was added dropwise under ice-cooling. The reaction mixture was stirred at room temperature for 24 hrs and was diluted with water. The aqueous solution was acidified with 1N-HCl and extracted with Chloroform. The organic layer was dried over Magnesium sulfate and concentrated. After column purification (Hexane+Ethyl acetate 1:1~Ethyl acetate+Acetone 3:1) Monomesylate was obtained. Yield 13.87 g (70%). The resulted Monomesylate was dissolved in Hexamethylphosphoric triamide (100 ml) with Lithium bromide (7.52 g) and stirred for 15.5 hrs at 50° C. The reaction mixture was diluted with Benzene, washed with water, brine and dried over Magnesium sulfate. The title compound was obtained after column purification (Hexane+Ethyl acetate 1:1). Yield 10.37 g (99%). NMR (CDCl$_3$): 2.49 (1H, br), 3.48–3.59 (4H, m), 3.88 (3H, s), 3.89 (3H, s), 3.95–4.14 (1H, m), 4.50 (2H, s). IR (Neat), cm$^{-1}$: 3445, 2910, 1589, 1505. [α]$^{25}_D$=–2.0° (C=2.0, Chloroform).

REFERENCE EXAMPLE 38

(2S)-1-Bromo-3-(3,4-dimethoxybenzyloxy)-2-[(4RS)-2-oxoazetidin-4-yl]-oxypropane (compound12, R$_2$=OCH$_2$C$_6$H$_3$(OCH$_3$)$_2$)

A mixture of reference example 37 (2.24 g, 4-Acetoxy azetidinone (2.40 g), Triethylamine (2.6 ml), Palladium acetate (170 mg) and dry Benzene (100 ml) was stirred at room temperature under Argon atmosphere for 24 hrs. After the reaction, resulted solid was removed by filtration, filtrate was washed with water, brine and dried over Magnesium sulfate. Column purification (Hexane+Ethyl acetate (1:1) gave the title compound. Yield: 2.65 g (76%). m.p. 66°~68° C. NMR (CDCl3): 2.91 (1H, d, J=15.7), 3.06–3.19 (1H, m), 3.32–3.42 (2H, m), 3.56–3.67 (2H, m), 3.85–3.95 (1H, m), 3.89 (3H, s), 3.90 (3H, m), 4.47 (2H, s), 5.16 (1H, dd, J=1.4, 4.3), 5.26 (1H, dd, J=1.4, 3.6), 6.46 (1H, br, s), 6.85 (1H, s). IR (Nujol), cm$^{-1}$: 3275, 1759, 1504. [α]$^{25}_D$=–9.0° (C=2.0, Chloroform).

REFERENCE EXAMPLE 39

(3RS, 5S)-3-(3,4-Dimethoxybenzyloxymethyl-4-oxa-1-azabicyclo [3,2,0]heptan-7-one (39A, (R=OCH$_2$C$_6$H$_3$(OCH$_3$)$_2$) and (3R,5R)-3-(3,4-Dimethoxybenzyloxymethyl)-4-oxa-1-azabicyclo[3,2,0] heptan-7-one (39B, R=OCH$_2$C$_6$H$_3$(OCH$_3$)$_2$)

A mixture of reference example 38 (2.44 g), Cesium carbonate (4.60 g) in Dimethyl sulfoxide (100 ml) was stirred at room temperature for 5 hrs. Reaction mixture was diluted with Ethyl acetate, washed with water, brine and dried over Magnesium sulfate. Column purification gave the title compounds. Yield: 39A 793 mg (42%), 39B 724 mg (38%). 39A: NMR (CDCl$_3$): 2.83 (1H, d, J=16.1), 2.85 (1H, dd, J=6.7, 10.8), 3.45–3.60 (2H, m), 3.89 (6H, s), 3.03 (1H, dd, J=6.7, 10.8), 4.51 (2H, s), 4.45–4.56 (1H, m), 5.34 (1H, d, J=2.6), 6.84 (2H, s), 6.87 (1H, s). IR (Neat), cm$^{-1}$: 2930, 1771, 1505. [α]$^{24}_D$: –95.0° (C=2.0, chloroform). 39B: NMR (CDCl$_3$): 2.87 (1H, d, J=16.0), 3.11 (1H, dd, J=7.3, 10.9), 3.24 (1H, dd, J=2.7, 16.0), 3.50 (2H, d, J=5.0), 3.62 (1H, dd, J=5.5, 11.0), 3.88 (3H, s), 3.91 (3H, s), 4.49 (2H, d, J=1.8), 4.43–4.56 (1H, m), 5.23 (1H, d, J=2.5), 6.84 (2H, s), 6.85 (1H, s). IR (Neat), cm$^{-1}$: 2925, 1770, 1505. [α]$^{24}_D$: +121.0° (C=2.0, Chloroform).

REFERENCE EXAMPLE 40

(3R,5S)-3-Hydroxymethyl-4-oxa-1-azabicyclo-[3,2,0]heptan-7-one

To a stirred solution of reference example 39A (1.08 g) in Dichloromethane (7 ml) and water (0.35 ml), 2.3-Dichloro-5,6-dicyano-1,4-benzoquinone (1.65 g) was added under ice-cooling condition and stirring was continued for 5 minutes. The reaction mixture was applied on column and eluted with Hexane+Ethyl acetate (1:1). Yield: 208 mg (40%). NMR (CDCl$_3$): 1.88 (1H, t, J=6.0), 2.86 (1H, d, J=16.1), 2.88 (1H, dd, J=7.5, 10.7), 3.31 (1H, dd, J=15.8, 3.1), 3.56–3.85 (2H, m), 3.94 (1H, dd, J=6.7, 11.6), 4.37–4.48 (1H, m), 5.36 (1H, d, J=2.7). IR (Neat), cm$^{-1}$: 3420, 1769. [α]$^{23}_D$=–169° (C=2.0, Chloroform).

REFERENCE EXAMPLE 41

(3RS,5SR)-3-Benzylthiomethyl-4-oxa-1-azabicyclo-[3,2,0]heptan-7-one (R=SCH$_2$C$_6$H$_5$)

To the mixture of Sodium hydride (60% oil dispersion, 120 mg) and dry Dimethyl formamide (5 ml), Benzyl mercaptane (373 mg) was added dropwise under ice-cooling and Nitrogen atmosphere. After the addition, the reaction mixture was stirred under the same condition for 1 hr. Then, the solution of reference example 2 (618 mg) in dry Dimethyl formamide (5 ml) was added dropwise under the same condition. The reaction mixture was stirred for 20 hrs. After the reaction, the mixture was diluted with Ethyl acetate, washed with water, brine and dried over Sodium sulfate. The reaction mixture was purified by column using Hexane and Ethyl acetate (2:1) as eluant. Yield: 624 mg (83%). NMR (CDCl$_3$): 2.52–2.75 (3H, m), 2.80–3.33 (2H, m), 3.77 (2H, s), 3.96 (1H, dd, J=6.1, 11.7), 4.30–4.43 (1H, m), 5.32 (1H, d, J=2.7), 7.31 (5H, m). IR (Neat), cm$^{-1}$: 3000, 1766, 1591.

REFERENCE EXAMPLE 42

(3RS,5SR)-3-Benzylsulfinylmethyl-4-oxa-1-azabicyclo[3,2,0]heptan-7-one (R=SOCH$_2$C$_6$H$_5$)

To the solution of (3RS, 5SR)-3-Benzylthiomethyl-4-oxa-1 -azabicyclo[3,2,0] heptan-7-one (926 mg) in Dichloromethane (10 ml), the solution of m-Chloroperbenzoic acid (72%, 755 mg) in Dichloromethane (30 ml) was added dropwise under ice-cooling and stirred at same condition for 1 hr. The reaction mixture was poured into aqueous Sodium hydrogen carbonate, extracted with Chloroform, and dried over Sodium sulfate. The reaction mixture was purified by column (Ethyl acetate+Acetone 5:1). Yield: 570 mg (58%). m.p. 80.5°~94.5° C. NMR (CDCl$_3$): 2.63–3.39 (5H, m), 4.03–4.15 (3H, m), 4.59–4.77 (1H, m), 7.26–7.40 (5H, m). IR (Nujol), cm$^{-1}$: 2940, 1706, 1494.

REFERENCE EXAMPLE 43

(3RS, 5SR)-3-Benzylsulfonylmethyl-4-oxa-1-azabicyclo-[3,2,0]heptan-7-one (R=SO$_2$CH$_2$C$_6$H$_5$)

Same as reference example 42, (3RS, 5SR)-3-Benzylthiomethyl-4 oxa-1-azabicyclo[3,2,0]heptan-7-one (295 mg) was oxidized with m-Chloroperbenzoic acid (72%, 437 mg) and the title compound was obtained as crystal. Yield: 166 mg (50%). m.p. 137°~145° C. IR (Nujol), cm$^{-1}$: 2930, 1777, 1454.

REFERENCE EXAMPLE 44

(3RS, 5SR)-3-Phenylthiomethyl-4-oxa-1-azabicyclo-[3,2,0]heptan-7-one (R=SC$_6$H$_5$)

Same as reference example 41, the title compound was obtained as oil. Yield: 299 mg (47%). m.p. 35.5°~37.0° C. NMR CDCl$_3$): 2.77 (1H, dd, J=7.5, 11.7), 2.83 (1H, d, J=16.1), 3.02 (1H, dd, J=7.3, 13.5), 3.18–3.32 (2H, m), 4.02 (1H, dd, J=6.5, 11.8), 4.38–4.50 (1H, m), 5.42 (1H, d, J=2.8), 7.18–7.42 (5H, m). IR (Neat), cm$^{-1}$: 2950, 1781.

REFERENCE EXAMPLE 45

(3RS, 5SR)-3-Phenylsulfinylmethyl-4-oxa-1-azabicyclo [3,2,0]heptan-7-one (R=SOC$_6$H$_5$)

Same as reference example 42, reference example 44 was oxidized to title compound. Yield: isomer 1; 97 mg (16%), isomer 2; 90 mg (15%). isomer 1: m.p. 150°~152.5° C. NMR CDCl$_3$): 2.65 (1H, dd, J=7.5, 11.9), 2.90–3.39 (3H, m), 4.04 (1H, dd, J=6.3, 12.0), 4.72–4.85 (1H, m), 5.40 (1H, d, J=2.7), 7.52–7.66 (5H, m). IR (Nujol), cm$^{-1}$: 2905, 1759, 1026. isomer 2: m.p. 119.0°~120.5° C. NMR (CDCl$_3$): 2.83 (1H, d, J=16.2), 2.88–3.06 (3H, m), 3.31 (1H, dd, J=2.9, 15.3), 4.06 (1H, dd, J=6.4, 11.9), 4.30–4.42 (1H, m), 5.39 (1H, d, J=2.7), 7.51–7.69 (5H, m). IR (Nujol), cm$^{-1}$: 2905, 1764, 1026.

REFERENCE EXAMPLE 46

(3RS, 5SR)-3-Phenylsulfonylmethyl-4-oxa-1-azabicyclo-[3,2,0]heptan-7-one (R=SO$_2$C$_6$H$_5$)

Same as reference example 42, reference example 44 was oxidized to title compound. Yield: 500 mg (88%). m.p. 144°~146° C. NMR (CDCl$_3$): 2.77 (1H, dd, J=7.3, 12.5), 2.85 (1H, d, J=16.0), 3.23–3.58 (2H, m), 4.12 (1H, dd, J=6.4, 12.2), 4.54–4.66 (1H, m), 5.26 (1H, d, J=2.7), 6.31–7.97 (5H, m). IR (Nujol), cm$^{-1}$: 2910, 1764, 1141.

REFERENCE EXAMPLE 47

1,4-Dibromo-2-(2-oxoazetidine-4-yloxy)butane (compound 5, X=Br, Y=CH$_2$Br)

A mixture of 1,4-dibromo-2-butanol (5.8 ml), 4-Acetoxyazetidinone (6.46 g), Palladium acetate (450 mg), Triethylamine (7 ml) and dry Benzene (75 ml) was stirred at room temperature under nitrogen for 23 hrs. Resulting solid was filtered off and filtrate was washed with water, brine and then dried over Magnesium sulfate. The residual oil, after evaporation, was purified by column chromatography using Hexane and Ethyl acetate (2:1) and the title compound was obtained. Yield: 5.88 g (78%). NMR (CDCl$_3$): 2.05–2.17 (2H, m), 2.87–3.27 (2H, m), 3.42–3.60 (4H, m), 3.90–4.02 (1H, m), 5.23–5.33 (1H, m), 6.53 (1H, br, s). IR (Neat), cm$^{-1}$: 3260, 1771.

REFERENCE EXAMPLE 48

(3RS, 5SR)-3-Bromoethyl-4-oxa-1-azabicyclo[3,2,0]-heptan-7-one (compound 8)

A mixture of reference example 47 (5.88 g), Cesium carbonate (9.58 g) and Dimethyl sulfoxide (200 ml) was stirred at room temperature for 6 hrs. Reaction mixture was diluted with Ethyl acetate and washed with water, brine and then dried over Magnesium sulfate. After column purification using Hexane and Ethyl acetate (3:1), the title compound was obtained as a mixture of diastereoisomers. Yield: 2.89 g (67%). NMR (CDCl$_3$): 1.76–1.99 (1H, m), 2.01–2.16 (1H, m), 2.85 (1H, d, J=15.1), 3.12–3.25 (2H, m), 3.51–3.84 (3H, m), 4.19–4.31 (1H, m), 5.16 (1H, d, J=3.2). IR (Neat), cm$^{-1}$: 2930, 1756.

REFERENCE EXAMPLE 49

(3RS, 5SR)-3-Formyloxyethyl-4-oxa-1-azabicyclo[3,2,0]-heptan-7-one (compound 9)

A mixture of reference example 43 (1.0 g), Sodium formate (610 mg), Potassium iodide (75 mg), Hexamethyl phosphoric triamide (5 ml) was stirred at 60° C. for 24 hrs. The reaction mixture was diluted with Ethyl acetate, washed with water, brine and dried over Magnesium sulfate. The residual oil, after evaporation, was purified chromatographically (Hexane+Ethyl acetate 3:1) and the title compound was obtained. Yield: 480 mg (58%). NMR (CDCl$_3$): 1.81–2.12 (2H, m), 2.64 (1H, dd, J=7.3, 11.7), 2.86 (1H, d, J=16.0), 3.15–3.47 (2H, m), 4.01 (1H, dd, J=6.0, 11.7), 4.20–4.70 (3H, m), 5.16 (1H, d, J=2.6), 5.32 (1H, d, J=2.5). IR (Neat), cm$^{-1}$: 2935, 1770, 1712.

REFERENCE EXAMPLE 50

(3RS, 5SR)-3-Hydroxyethyl-4-oxa-1-azabicyclo[3,2,0]-heptan-7-one (compound 10)

A mixture of reference example 49 (400 mg), Sodium hydrogen carbonate (363 mg), Methanol (5 ml) was stirred at room temperature for 5 minutes. Solid was filtered off with suction and the filtrate was evaporated. Resulting oil was purified by flash column chromatography by gradient elution using Hexane and Ethyl acetate. The title compound was obtained as an oily mixture of two diastereoisomers. Yield: 194 mg (57%). NMR (CDCl$_3$): 1.79–2.17 (2H, m), 2.65 (1H, dd, J=7.4, 1.7), 2.86 (1H, dd, J=2.2, 15.8), 3.15–3.48 (3H, m), 3.81 (3H, t, J=5.2), 4.02 (1H, dd, J=6.2, 11.7), 5.16 (1H, d, J=2.6), 5.34 (1H, d, J=2.7). IR (Neat), cm$^{-1}$: 3425, 1768.

REFERENCE EXAMPLE 51

(3RS, 5SR)-3-(4-Methylbenzenesulfonyl)methyl-4-oxa-1-azabicyclo[3,2,0]heptan-7-one
($R=SO_2C_6H_5$—$CH_3$)

According to the same procedure described in reference example 46, title compound was obtained as solid. Yield: 30 mg (11%). m.p. 120°~121° C. NMR ($CDCl_3$): 2.50 (3H, s), 2.76 (1H, dd, J=7.3, 12.0), 2.84 (1H, d, J=16.4), 3.20–3.35 (2H, m), 3.51 (1H, dd, J=5.9, 14.1), 4.10 (1H, dd, J=6.3, 12.2), 4.50–4.63 (1H, m), 5.27 (1H, d, J=2.8), 7.38 (2H, d, J=8.2), 7.80 (2H, d, J=8.2). IR (Nujol), $cm^{-1}$: 2910, 1769, 1141.

TEST EXAMPLE 1

In Vitro KB Cell Cytotoxicity Assay

In vitro KB cell cytotoxicity assay was done by modification of the crystal violet assay (Grillis et al., Anal Biochem., 159, 109–113 (1986)).

KB cells were cultivated in Eagles minimum essential medium supplemented with 10% calf serum and incubated at 37° C. in a humidified 5% $CO_2$ atmosphere to prepare a cell stock. Cells were counted using a neubauer hemocytometer and seeded in 96 well plates at 100 µl of $3\times10^4$ cells/ml and cultured for one day. Test compounds were diluted and 100 µl of the solution was added in triplicate wells to give final concentration of 10, 5, 1, 0.5 and 0.1 µg/ml. Control wells were identical except that test compound was absent. These were cultured for three days. Then the cells were fixed with addition of 20 µl of 25% glutaraldehyde for 15 minutes, washed with water and dried. Then stained with 100 µl of 0.05% crystal violet for 15 minutes, washed with water and dried. The wells were eluted with 100 µl of 0.05M $NaH_2PO_4$/ethanol (1:1 v/v) and read at $OD_{540}$ on a multiscan spectrophotometer. $TD_{50}$ values were calculated using the following formula.

% Inhibition Greater than 50%—50%

% inhibition greater than 50%—% inhibition less than 50% to give the interpolative value between two dilutions.

The compound of formula (I) was assayed by this method against KB cell lines and their $TD_{50}$ values are reported in Table 1.

TEST EXAMPLE 2

In Vitro L1210 Cell Cytotoxicity Assay

In vitro L1210 cell cytotoxicity assay was done by the method of microculture tetrazolium assay (Alley et al., Cancer Research, 48, 589–601 (1988)).

L1210 cells were cultivated in RPMI 1640 medium supplemented with 10% fetal calf serum and 50 µl of 2-mercaptoethanol at 37° C. in humidified 5% $CO_2$ atmosphere to prepare a cell stock. Cells were counted using neubauer hemocytometer and seed in 96 well plates at 100 µl of $0.5\times10^4$ cells per ml. The test compounds were diluted and 100 µl of the solution was added in triplicate wells to give the final concentration of 10, 5, 1, 0.5 and 0.1 µg/ml. Control wells were identical except that the test compound was absent. These were cultured for three days. Results were assayed using the microculture tetrazolium assay briefly. 50 µl of MTT formazoan working solution (1:5 v/v in culture medium) was added to each well and cultures were incubated at 37° C. for 4 hrs. Culture plates were centrifuged at low speed for 5 minutes. All but 10–20 µl of culture medium supernatant was removed by slow aspiration and replaced by 50 µl of DMSO. The formazoan was dissolved by shaking on a mechanical shaker and read at $OD_{540}$ on a multiscan spectrophotometer. $TD_{50}$ values were calculated using the formula:

$$\frac{\% \text{ inhibition greater than } 50\% - 50\%}{\% \text{ inhibition greater than } 50\% - \% \text{ inhibition less than } 50\%}$$

to give interpolative values between two dilutions.

The compounds of formula (I) were assayed by this method against L-1210 cell lines and the $TD_{50}$ values are summarized in Table 1.

TABLE 1

In Vitro Cell Toxicity of Compound of General Formula (I)

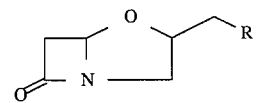

| Reference Example No. | R | Cytotoxicity $TD_{50}$ µg/ml KB | L1210 |
|---|---|---|---|
| 3 | OCHO | 0.04 | 0.22 |
| 4 | $OCOCH_3$ | 0.4 | 0.4 |
| 5 | $OCO(CH_2)_2CH_3$ | 0.3 | 0.45 |
| 6 | $OCO(CH_2)_4CH_3$ | 0.3 | 0.70 |
| 7 | $OCO(CH_2)_6CH_3$ | 0.1 | 0.34 |
| 8 | $OCO(CH_2)_8CH_3$ | 0.3 | 0.37 |
| 9 | $OCOCH(CH_3)_2$ | 0.4 | — |
| 10 | $OCOCH_2CH(CH_3)_2$ | 0.25 | — |
| 11 | $OCO(CH_2)_2CH(CH_3)_2$ | 0.4 | — |
| 12 | $OCOCH(CH_3)(CH_2)_3CH_3$ | 0.4 | — |
| 13 | $OCOCH_2Cl$ | 0.5 | 0.28 |
| 14 | $OCOCH=CHCH=CHCH_3$ | 0.3 | 0.65 |
| 15 | $OCO(CH_2)_7(CH=CHCH_2)_3CH_3$ | 0.41 | 0.5 |
| 16 | $OCOC\equiv CH$ | 0.07 | 0.04 |
| 17 | $OCO(CH_2)_2C\equiv CH$ | 0.27 | — |
| 18 | $OCOC_6H_5$ | 5.0 | — |
| 19 | $OCOC_6H_2(2,4,6\text{-}CH_3)$ | 2.0 | — |
| 20 | $OCOC_6H_4OCH_3(4)$ | 0.6 | — |
| 21 | $OCOC_6H_4OH(4)$ | 2.2 | — |
| 22 | $OCOC_6H_4(3,4\text{-}OH)$ | 2.5 | — |
| 23 | $OCOC_6H_4OCH_2CO_2Na(4)$ | 8.7 | — |
| 24 | $OCO\text{-}c\text{-}C_6H_{10}CO_2Na(2)$ | 0.7 | — |
| 25 | $OCOC_6H_4CO_2Na(2)$ | 1.5 | — |
| 26 | $OCOCH_2CH_2COONa$ | 9.8 | — |
| 27 | $OCOCH=CH\text{-}COONa$ | 2.4 | — |
| 28 | $OCOCH(OH)CH_2COOCH_2\text{-Clavam}$ | 0.3 | — |
| 29 | $OCOCH(OH)CH(OH)COOCH_2\text{-Clavam}$ | 0.3 | — |
| 30 | $OCOCH=CHCOOCH_2\text{-Clavam}$ | 0.05 | — |
| 31 | $OCOC_6H_4F(4)$ | 0.4 | — |
| 32 | $OCOC_6H_2(2,4,5\text{-F})$ | 0.3 | — |
| 33 | $OCOC_6H_4CN(4)$ | 0.3 | — |
| 34 | $OCOC_6H_4NH_2(4)$ | 0.4 | — |
| 35 | $OCOC_6H_2(3\text{-}OCH_3,4\text{-}OH,5\text{-}OCH_3)$ | 0.8 | — |
| 39A | $OCH_2C_6H_3(3,4\text{-}OCH_3)$ | 0.56 | — |
| 39B | $OCH_2C_6H_3(3,4\text{-}OCH_3)$ | 0.57 | — |
| 40 | OH(3R,5S) | 0.03 | 0.027 |
| 41 | $S\text{-}CH_2C_6H_5$ | 5.0 | — |
| 42 | $SOCH_2C_6H_5$ | 0.1 | 0.3 |
| 43 | $SO_2CH_2C_6H_5$ | 0.5 | — |
| 44 | $S\text{-}C_6H_5$ | 3.0 | — |
| 45 | $SOC_6H_5$ | 0.3 | 0.26 |
| 46 | $SO_2C_6H_5$ | 2.0 | — |
| 50 | $CH_2OH$ | 0.7 | — |
| 51 | $SO_2C_6H_4\text{-}CH_3(4)$ | 1.0 | — |

(—) Not Done

TEST EXAMPLE 3

In Vivo Antitumor Activity Against Sarcoma 180

The compound of general formula (I) were tested in vivo against Sarcoma 180 xenografted tumor to mice as illustrated herein after.

Sarcoma 180, $5 \times 10^6$ cells were inoculated by S.C. to male ICR mice (6 weeks old) on day 0. Drugs were administered on days 1, 5 and 9. Mice were killed and tumor weight was measured on day 12 after transplantation. The percentage inhibition of tumor growth was calculated from the mean tumor weight of the treated group compared with that of the control group. Number of mice used in each group was between 6 to 10. The percentage inhibition of tumor Sarcoma 180 group by compound of formula (I) are summarized in Table 2.

TABLE 2

Effect of Compounds of Formula (I) against Sarcoma 180
(s.c. - i.p.) in Male ICR

| Reference Example No. | Dose mg/kg/day | Mortality in 12 days | % Inhibition |
|---|---|---|---|
| 3 | 6.25 | 0/7 | 55.3 |
|  | 3.13 | 0/7 | 27.6 |
| 4 | 12.5 | 0/7 | 70.7 |
|  | 6.25 | 0/7 | 64.0 |
| 6 | 50 | 0/6 | 78.0 |
|  | 25 | 0/6 | 61.4 |
|  | 13 | 0/6 | 36.4 |
| 16 | 3.13 | 0/7 | 53.0 |
|  | 1.56 | 0/7 | 45.9 |
| 20 | 25 | 0/7 | 74.1 |
|  | 12.5 | 0/7 | 59.1 |
|  | 6.25 | 0/7 | 68.6 |
|  | 3.13 | 0/7 | 60.0 |
| 21 | 50 | 0/6 | 48.3 |
| 23 | 50 | 0/6 | 23.7 |
| 25 | 100 | 2/6 | 44.1 |
| 30 | 25 | 0/6 | 76.9 |
|  | 12.5 | 0/6 | 34.0 |
| 31 | 25 | 0/7 | 69.4 |
|  | 12.5 | 0/7 | 53.2 |
| 40 | 7.5 | 0/7 | 77.4 |
|  | 3.75 | 0/7 | 69.1 |
|  | 1.88 | 0/7 | 63.7 |
|  | 0.94 | 0/7 | 56.1 |
| 41 | 6.25 | 0/6 | 17.1 |
| 42 | 50 | 0/7 | 64.0 |
| 43 | 12.5 | 0/6 | 19.5 |
| 50 | 50 | 0/6 | 65.3 |

What we claim is:

1. A method for treating solid cancers and leukemia, comprising administering to a mammal in need of such treatment an anti-tumor effective amount of a composition comprising an effective amount of a 4-oxa-1-azabicyclo [3,2,0] heptan-7-one derivative according to formula (I) or a pharmaceutically acceptable salt thereof

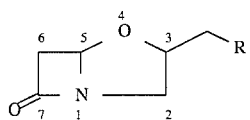

wherein R is:

—$OCOR_1$, wherein $R_1$ is a hydrogen atom, a $C_{1-9}$ alkyl group which is unsubstituted or substituted by either one or two substituents selected together from halogen atom, hydroxy, carboxy group or (3RS, 5SR)-(4oxa-1azabicyclo[3,2,0]heptan-7-one-3-yl) methyloxycarbonyl, a $C_{2-17}$ alkenyl group which is unsubstituted or substituted by carboxy group or (3RS, 5SR)-4-oxa-1-azabicyclo[3,2,0]heptan-7-one-3-yl)methyloxycarbonyl, a $C_{2-4}$ alkynyl group, a $C_{3-6}$ cycloalkyl group which is unsubstituted or substituted by carboxy group or phenyl group which may have 1, 2 or 3 substituents selected from the group consisting of cyano group, halogen atom, carboxy group, $C_{1-6}$ alkoxy group which is unsubstituted or substituted by carboxy group, $C_{1-6}$ alkyl group, amino group or hydroxy group;

—$OR_2$, wherein $R_2$ is a hydrogen atom or benzyl group which is unsubstituted or substituted by 1 or 2 $C_{1-6}$ alkoxy group;

—$S(O)_nR_3$, wherein $R_3$ is phenyl group or a benzyl group which is unsubstituted or substituted by $C_{1-6}$ alkyl group, n is 0, 1 or 2; or —$CH_2OH$, and a pharmaceutically acceptable carrier.

2. The method according to claim 1, wherein said solid cancers are selected from the group consisting of stomach cancer, lung cancer, breast cancer, liver cancer, and uterine cancer.

3. The method according to claim 1, wherein said solid cancers and leukemia are selected from the group consisting of nasopharyngeal carcinoma, gastric cancer, lymphocytic leukemia, soft tissue solid tumors, lung fibroblastoma and colon cancer.

4. The method according to claim 1 wherein R in said 4-oxa-1-azabicyclo [3,2,0] heptan-7-one derivative according to formula (I) is —$OCOR_1$, and wherein $R_1$ is selected from the group consisting of hydrogen, methyl, propyl, 1-methylethyl, 2-methylpropyl, pentyl, 1-methylbutyl, 3-methylbutyl, hexyl, heptyl, chloromethyl, 2-carboxyethyl, 1-hydroxy-2-[(3RS,5SR)-4-oxa-1-azabicyclo [3,2,0]heptan-7-one-3-yl)methyloxycarbonyl]ethyl, 1,2-dihydroxy-2-[(3RS, 5SR)-(4-oxa-1-azabicyclo[3,2,0]heptan-7-one-3-yl)methyloxycarbonyl]ethyl, 1,3-pentadienyl, 8, 11, 14-heptadecatrienyl, 2-carboxyethenyl, 2[(3RS, 5SR)-(4-oxa-1-azabicyclo[3,2,0]heptan-7-one-3-yl)methyloxycarbonyl] ethenyl, ethynyl, 3-butynyl, phenyl, 2,4,6-trimethylphenyl, 4-methoxyphenyl, 4-hydroxyphenyl, 3,4-dihydroxyphenyl, 2-carboxyphenyl, 4-(carboxymethyloxy)phenyl, 4-fluorophenyl, 2,4,5-trifluorophenyl, 4-cyanophenyl, 4-aminophenyl, 4-hydroxy-3,5-dimethoxyphenyl and 2-carboxycyclohexyl.

5. The method according to claim 1, wherein R in said 4-oxa-1-azabicyclo [3,2,0] heptan-7-one derivative according to formula (I) is $OR_2$, and wherein $R_2$ is selected from the group consisting of hydrogen, 4-methoxybenzyl and 3,4-dimethoxybenzyl.

6. The method according to claim 1, wherein R in said 4-oxa-1-azabicyclo [3,2,0]heptan-7-one derivative according to formula (I) is $S(O)_nR_3$, $R_3$ is a phenyl group or a benzyl group which is unsubstituted or substituted by a $C_{1-3}$ alkyl group, and n is 0, 1 or 2.

* * * * *

UNITED STATES PATENT AND TRADEMARK OFFICE
CERTIFICATE OF CORRECTION

PATENT NO. : 5,561,126
DATED : October 1, 1996
INVENTOR(S) : OTANI et al.

It is certified that error appears in the above-indentified patent and that said Letters Patent is hereby corrected as shown below:

TITLE PAGE

Item [75], line [2], please delete "Iokushima" insert therefor -- Tokushima --.

Signed and Sealed this

Twenty-first Day of January, 1997

Attest:

BRUCE LEHMAN

*Attesting Officer*    *Commissioner of Patents and Trademarks*